United States Patent [19]

Schaar

[11] 4,066,081
[45] Jan. 3, 1978

[54] DIAPER WITH EXTENSIBLE FASTENER

[75] Inventor: Charles H. Schaar, Lake Zurich, Ill.

[73] Assignee: Colgate-Palmolive Company, New York, N.Y.

[21] Appl. No.: 742,973

[22] Filed: Nov. 18, 1976

[51] Int. Cl.² .................. A41B 13/02; A61F 13/16
[52] U.S. Cl. ................................. 128/287; 128/284
[58] Field of Search .............. 128/284, 287, 286, 291; 24/73 VA, 67, DIG. 11

[56] References Cited

U.S. PATENT DOCUMENTS

| 3,800,796 | 4/1974 | Jacob | 128/284 |
|---|---|---|---|
| 3,920,018 | 11/1975 | Schaar | 128/287 |
| 3,926,190 | 12/1975 | Tritsch | 128/287 |
| 3,930,503 | 1/1976 | Tritsch | 128/287 |

*Primary Examiner*—Aldrich F. Medbery
*Attorney, Agent, or Firm*—Powell L. Sprunger

[57] ABSTRACT

A disposable diaper comprising, an absorbent pad assembly having opposed surfaces and a side edge. The diaper has a tape fastener comprising, a pressure-sensitive tape strip having a first end portion secured to one of the surface of the pad assembly adjacent a side edge, a second securement end portion for securing the diaper about an infant, and an elastic band extending around and laterally constraining a central portion of the strip intermediate the first and second portions. The band reduces the lateral dimensions of the central portion and the effective normal length of the strip, such that the second strip portion is longitudinally extensible relative the first portion by increasing the size of the central portion from reduced to enlarged lateral dimensions while expanding the band responsive to forces applied in a longitudinal direction against the strip.

4 Claims, 4 Drawing Figures

DIAPER WITH EXTENSIBLE FASTENER

BACKGROUND OF THE INVENTION

The present invention relates to absorbent articles, and more particularly to disposable diapers.

Before the present invention, a various assortment of disposable diapers have been proposed for use on infants. The diapers are normally constructed with a fluid impervious backing sheet, a fluid pervious top sheet, and an absorbent pad intermediate the backing and top sheets. Diapers have also been provided with tape fasteners for use in securing the diapers about an infant. However, most fasteners have been relatively inextensible, and it has been found that such inextensible fasteners cause frequent tearing or rupturing of the tapes from the diaper backing sheet when forces are applied to the fasteners during placement or use of the diapers. Alternatively, proposed fasteners, such as rubber, may be too extensible and may result in a loose fitment of the diaper about the infant.

SUMMARY OF THE INVENTION

A principal feature of the present invention is the provision of an improved fastener for a disposable diaper.

The diaper comprises an absorbent pad assembly having opposed surfaces and a side edge. The tape fastener of the invention comprises a pressure-sensitive tape strip having a first end portion secured to one of the surfaces of the pad assembly adjacent the side edge, a second securement end portion for securing the diaper about an infant, and an elastic band extending around and laterally constraining a central portion of the strip intermediate the first and second portions, with the band reducing the lateral dimensions of the central portion and the effective normal length of the strip.

A feature of the present invention is that the size of the central portion increases from reduced to enlarged lateral dimensions while expanding the band responsive to forces applied in a longitudinal direction against the strip.

Thus, another feature of the invention is that the second strip portion is longitudinally extensible relative the first portion of the tape strip.

Yet another feature of the invention is that the extensible strip minimizes the possibility that the tape strip may tear from a backing sheet of the diaper during placement and use of the diaper.

Still another feature of the invention is that the backing of the tape strip is relatively inextensible and prevents over-extension of the tape strip.

Further features will become more fully apparent in the following description of the embodiments of this invention and from the appended claims.

DESCRIPTION OF THE PREFERRED EMBODIMENTS

Figure 1:
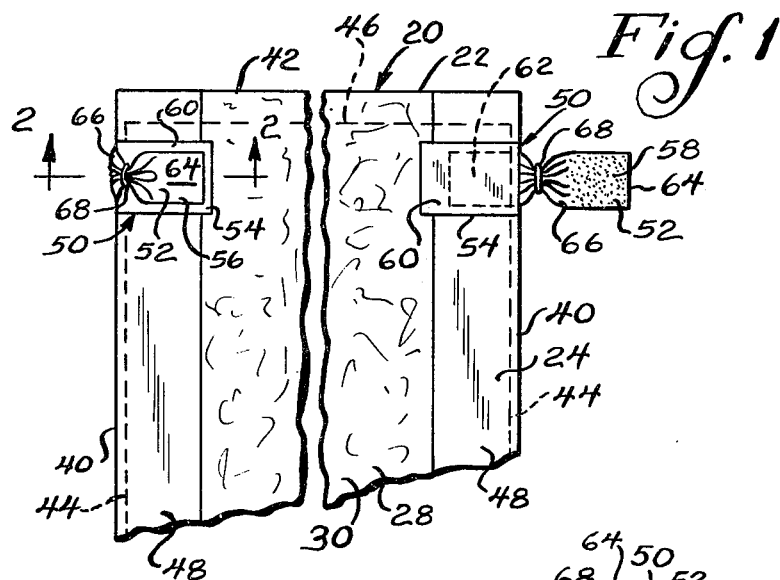
FIG. 1 is a fragmentary front plan view of a disposable diaper having a tape fastener of the present invention.
Figure 2:
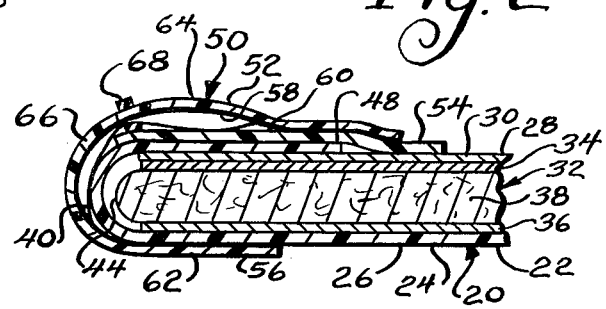
FIG. 2 is a fragmentary sectional view taken substantially as indicated along the line 2—2 of FIG. 1.

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly, a fluid pervious cover or top sheet 28 defining a substantial part of a front surface 30 of the pad assembly 22, and an absorbent pad 32 located between the backing sheet 24 and top sheet 28. The pad 32 may have a front wadding sheet 34, a back wadding sheet 36, and a pad portion 38, such as comminuted wood pulp termed in the art as fluff, located between the front and back wadding sheets 34 and 36 which serve to increase the structural integrity of the pad portion 38. The pad assembly 22 has a pair of side edges 40 and a pair of end edges 42 connecting the side edges 40. The pad 32 also has a pair of side edges 44 and a pair of end edges 46 connecting the pad side edges 44. In a preferred form, as shown, lateral side margins 48 of the backing sheet 24 are folded over the front of the diaper and are secured to the top sheet 28, such that the side margins 48 of the backing sheet 24 cover lateral side margins of the pad 32. If desired, the pad assembly 22 may be folded into a box-pleat configuration along a plurality of longitudinally extending fold lines.

The diaper 20 also has a pair of tape fasteners generally designated 50 comprising a pair of pressure-sensitive tape strips 52 and a pair of release sheets 54. Each tape strip 52 has a relatively inextensible backing 56, such a paper, and a suitable adhesive 58 on a front surface of the backing 56. As shown, the release sheets 54 are fixedly secured to the front surface 30 of the pad assembly 22 adjacent the respective side edges 40, and have outer release surfaces 60 which may be defined by suitable treatment of the release sheets or by the material of the release sheets themselves, e.g., the release sheets may comprise paper strips having a silicone release coating or strips of polyethylene.

Each tape strip 52 has a first end portion 62 attached to the back surface 26 of the pad assembly 22 adjacent the respective side edge 40, a second securement end portion 64, and a central portion 66 intermediate the first and second end portions 62 and 64 adjacent the side edge 40 of the pad assembly 22. Each fastener 50 also has an endless elastic band 68, such a rubber, extending around and laterally constraining the central portion 66 of the tape strip 52, such that the band 68 gathers the central strip portion 66 and reduces its lateral dimensions while also reducing the effective normal length of the tape strip 52. In the packaged configuration of the diaper 20, the tape strips 52 are folded around the side edges 40 of the pad assembly 22, and the securement end portions 64 of the tape strips 52 are releasably attached to the release surface 60 of the associated release sheets 54, as shown in the left-hand portion of FIG. 1 and in FIG. 2.

Figure 3:
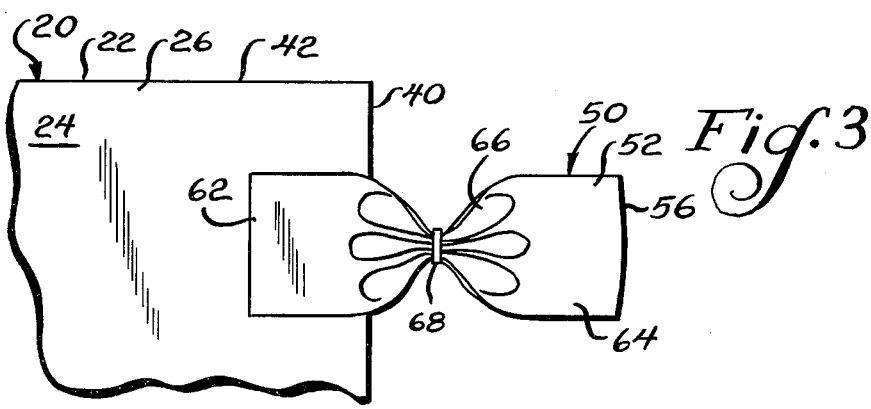
FIG. 3 is a fragmentary back plan view of the diaper of FIG. 1 illustrating the tape fastener in a normal configuration.
Figure 4:
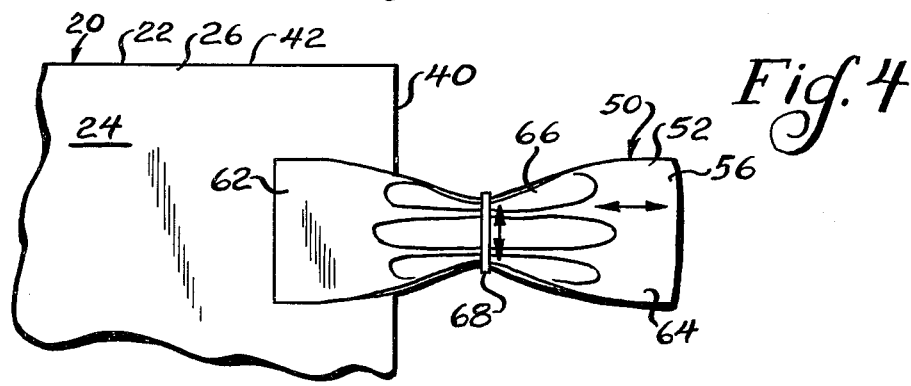
FIG. 4 is a fragmentary back plan view of the diaper of FIG. 3 illustrating the tape fastener in an extended configuration.

When it is desired to place the diaper about an infant, the securement portions 64 of the tape strips 52 may be peeled from the release sheets 54 and are folded into a configuration extending past the side edges 40 of the pad assembly 22, as shown in the right-hand portion of FIG. 1 and in FIG. 3. Next, the securement portions 64 of the tape strips 52 are attached to a remote portion of the diaper in order to secure the diaper about the infant. With reference to FIG. 4, when forces are applied against the tape strips 52 in a longitudinal direction of the strips, the second strip portions 64 extend relative the first strip portions 62 and the size of the central strip portions 66 increase from reduced to enlarged lateral dimensions while the elastic bands 68 expand responsive to enlargment of the central strip portions 66. Thus, the central portion 66 of each tape strip 52 expands from its reduced lateral dimensions, as shown in FIG. 3, into enlarged lateral dimensions with the band 68 expanded, as shown in FIG. 4, in order to permit longitudinal extension of the tape strip 52. When tension on the band 68 is removed, the expanded band 68 again gathers the central strip portion 66 into its reduced lateral dimensions, as shown in FIG. 3, and reduces the effective length of the strip 52. Thus, the tape strips 52 are longitudinally extensible to a slight degree in order to absorb or cushion forces and shocks applied to the tape strips and prevent rupture and tearing of the tape strips from the diaper backing sheet 24 during placement and use of the diaper. In addition, the relatively inextensible backings 56 of the tape strips 52 prevent over-extension of the tape strips and minimize the possibility of a loose fitment of the diaper about the infant.

The foregoing detailed description is given for clearness of understanding only, and no unnecessary limitations should be understood therefrom, as modifications will be obvious to those skilled in the art.

I claim:

1. A disposable diaper, comprising:
   an absorbent pad assembly having opposed surfaces and a side edge; and
   a tape fastener, comprising a pressure-sensitive tape strip having a first end portion secured to one of said surfaces of the pad assembly adjacent the side edge, a second securement end portion for securing the diaper about an infant, a means for providing a stress extensible diaper fastening means comprising an elastic band extending around and laterally constraining a central portion of the strip intermediate said first and second portions, with said band being of a size to constrict and reduce the lateral dimensions of said central portion and thus the effective normal length of said strip, and with said second strip portion being longitudinally extensible relative the first portion by increasing the size of said central portion from reduced to enlarged lateral dimensions while expanding said band responsive to forces applied in a longitudinal direction against said strip.

2. The diaper of claim 1 including a release sheet releasably attached to adhesive on said securement portion.

3. The diaper of claim 2 wherein said first strip portion is secured to a back surface of the pad assembly, said release sheet is secured to a front surface of the pad assembly, and said strip is folded around said side edge.

4. The diaper of claim 1 wherein said central portion extends past the side edge of the pad assembly.

* * * * *